(12) United States Patent
Saltsman et al.

(10) Patent No.: US 7,419,638 B2
(45) Date of Patent: Sep. 2, 2008

(54) MICROFLUIDIC DEVICES FOR FLUID MANIPULATION AND ANALYSIS

(75) Inventors: Patrick Saltsman, Seattle, WA (US);
Mingchao Shen, Edmonds, WA (US);
Jeffrey M Houkal, Bellevue, WA (US);
Christy A Lancaster, Seattle, WA (US);
C. Frederick Battrell, Redmond, WA (US); Bernhard H Weigl, Seattle, WA (US)

(73) Assignee: Micronics, Inc., Redmond, WA (US)

( * ) Notice: Subject to any disclaimer, the term of this patent is extended or adjusted under 35 U.S.C. 154(b) by 889 days.

(21) Appl. No.: 10/870,717

(22) Filed: Jun. 17, 2004

(65) Prior Publication Data

US 2005/0106066 A1 May 19, 2005

Related U.S. Application Data

(63) Continuation-in-part of application No. 10/757,767, filed on Jan. 14, 2004, now abandoned.

(60) Provisional application No. 60/441,873, filed on Jan. 21, 2003, provisional application No. 60/439,825, filed on Jan. 14, 2003.

(51) Int. Cl.
*B01L 3/02* (2006.01)
*G01N 21/00* (2006.01)

(52) U.S. Cl. .......................... 422/100; 422/57; 422/58; 422/59; 422/68.1

(58) Field of Classification Search ................. 422/100, 422/57–59, 68.1; 436/180, 164–165
See application file for complete search history.

(56) References Cited

U.S. PATENT DOCUMENTS

| | | | | |
|---|---|---|---|---|
| 3,640,267 | A |  | 2/1972 | Hurtig et al. ................... 128/2 |
| 3,799,742 | A |  | 3/1974 | Coleman ................... 23/253 R |
| 5,387,526 | A | * | 2/1995 | Garner et al. ............... 436/169 |
| 5,731,212 | A | * | 3/1998 | Gavin et al. ................. 436/526 |
| 5,788,927 | A | * | 8/1998 | Farrell et al. .................. 422/63 |
| 5,863,502 | A |  | 1/1999 | Southgate et al. ............. 422/58 |
| 6,040,193 | A | * | 3/2000 | Winkler et al. ................ 506/16 |
| 6,451,610 | B1 | * | 9/2002 | Gorman et al. ............... 436/69 |
| 6,752,966 | B1 | * | 6/2004 | Chazan ....................... 422/102 |
| 6,852,284 | B1 | * | 2/2005 | Holl et al. .................. 422/68.1 |
| 7,226,562 | B2 | * | 6/2007 | Holl et al. .................. 422/68.1 |
| 7,312,085 | B2 | * | 12/2007 | Chou et al. ................... 436/43 |

(Continued)

FOREIGN PATENT DOCUMENTS

EP 1203959 A1 5/2002

(Continued)

OTHER PUBLICATIONS

Gravesen, P. et al., "Microfluidics—a review," *Journal of Micromechanics and Microengineering* 3: 168-182, 1993.

*Primary Examiner*—Brian R. Gordon
(74) *Attorney, Agent, or Firm*—Seed IP Law Group PLLC

(57) ABSTRACT

The present invention relates to microfluidic devices and methods for manipulating and analyzing fluid samples. The disclosed microfluidic devices utilize a plurality of microfluidic channels, inlets, valves, filter, pumps, liquid barriers and other elements arranged in various configurations to manipulate the flow of a fluid sample in order to prepare such sample for analysis.

8 Claims, 15 Drawing Sheets

U.S. PATENT DOCUMENTS

| | | | |
|---|---|---|---|
| 2001/0027745 A1 | 10/2001 | Weigl et al. ................ 117/206 |
| 2002/0022261 A1 | 2/2002 | Anderson et al. ........ 435/287.2 |
| 2002/0037499 A1* | 3/2002 | Quake et al. .................... 435/5 |
| 2002/0155010 A1 | 10/2002 | Karp et al. ............... 417/413.2 |
| 2002/0164816 A1* | 11/2002 | Quake ......................... 436/161 |
| 2003/0185713 A1* | 10/2003 | Leonard et al. ............. 422/100 |
| 2004/0115838 A1* | 6/2004 | Quake et al. ................ 436/538 |
| 2004/0224425 A1* | 11/2004 | Gjerde et al. ............... 436/518 |
| 2005/0084421 A1* | 4/2005 | Unger et al. ................ 422/100 |
| 2005/0129581 A1* | 6/2005 | McBride et al. ............ 422/100 |
| 2006/0094119 A1* | 5/2006 | Ismagilov et al. ............. 436/53 |
| 2006/0099116 A1* | 5/2006 | Manger et al. .............. 422/100 |
| 2006/0245978 A1* | 11/2006 | Prins .......................... 422/100 |
| 2007/0166199 A1* | 7/2007 | Zhou et al. .................. 422/100 |
| 2007/0280856 A1* | 12/2007 | Ulmanella et al. .......... 422/100 |

FOREIGN PATENT DOCUMENTS

| | | |
|---|---|---|
| EP | 1240945 A2 | 9/2002 |
| WO | WO 01/26813 | 4/2001 |
| WO | WO 01/75415 | 10/2001 |
| WO | WO 2004/065930 | 8/2004 |

\* cited by examiner

MICROFLUIDIC DEVICES FOR FLUID MANIPULATION AND ANALYSIS

CROSS-REFERENCE TO RELATED APPLICATIONS

This application is a continuation-in-part of U.S. patent application Ser. No. 10/757,767, filed Jan. 14, 2004, which claims the benefit of U.S. Provisional Patent Application Nos. 60/439,825, filed Jan. 14, 2003, and 60/441,873, filed Jan. 21, 2003, all of which applications are hereby incorporated by reference in their entirety.

BACKGROUND OF THE INVENTION

1. Field of the Invention

The present invention relates generally to microfluidic devices and analysis methods, and, more particularly, to microfluidic devices and methods for the manipulation and analysis of fluid samples.

2. Description of the Related Art

Microfluidic devices have become popular in recent years for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition and processing of information.

The ability to perform analyses microfluidically provides substantial advantages of throughput, reagent consumption, and automatability. Another advantage of microfluidic systems is the ability to integrate a plurality of different operations in a single "lap-on-a-chip" device for performing processing of reactants for analysis and/or synthesis.

Microfluidic devices may be constructed in a multi-layer laminated structure wherein each layer has channels and structures fabricated from a laminate material to form microscale voids or channels where fluids flow. A microscale or microfluidic channel is generally defined as a fluid passage which has at least one internal cross-sectional dimension that is less than 500 μm and typically between about 0.1 μm and about 500 μm.

U.S. Pat. No. 5,716,852, which patent is hereby incorporated by reference in its entirety, is an example of a microfluidic device. The '852 patent teaches a microfluidic system for detecting the presence of analyte particles in a sample stream using a laminar flow channel having at least two input channels which provide an indicator stream and a sample stream, where the laminar flow channel has a depth sufficiently small to allow laminar flow of the streams and length sufficient to allow diffusion of particles of the analyte into the indicator stream to form a detection area, and having an outlet out of the channel to form a single mixed stream. This device, which is known as a T-Sensor, allows the movement of different fluidic layers next to each other within a channel without mixing other than by diffusion. A sample stream, such as whole blood, a receptor stream, such as an indicator solution, and a reference stream, which may be a known analyte standard, are introduced into a common microfluidic channel within the T-Sensor, and the streams flow next to each other until they exit the channel. Smaller particles, such as ions or small proteins, diffuse rapidly across the fluid boundaries, whereas larger molecules diffuse more slowly. Large particles, such as blood cells, show no significant diffusion within the time the two flow streams are in contact.

Typically, microfluidic systems require some type of external fluidic driver to function, such as piezoelectric pumps, micro-syringe pumps, electroosmotic pumps, and the like. However, in U.S. patent application Ser. No. 09/684,094, which application is assigned to the assignee of the present invention and is hereby incorporated by reference in its entirety, microfluidic systems are described which are completely driven by inherently available internal forces such as gravity, hydrostatic pressure, capillary force, absorption by porous material or chemically induced pressures or vacuums.

In addition, many different types of valves for use in controlling fluids in microscale devices have been developed. For example, U.S. Pat. No. 6,432,212 describes one-way valves for use in laminated microfluidic structures, U.S. Pat. No. 6,581,899 describes ball bearing valves for use in laminated microfluidic structures, and U.S. patent application Ser. No. 10/114,890, which application is assigned to the assignee of the present invention, describes a pneumatic valve interface, also known as a zero dead volume valve, for use in laminated microfluidic structures. The foregoing patents and patent applications are hereby incorporated by reference in their entirety.

Although there have been many advances in the field, there remains a need for new and improved microfluidic devices for manipulating and analyzing fluid samples. The present invention addresses these needs and provides further related advantages.

BRIEF SUMMARY OF THE INVENTION

In brief, the present invention relates to microfluidic devices and methods for manipulating and analyzing fluid samples. The disclosed microfluidic devices utilize a plurality of microfluidic channels, inlets, valves, filters, pumps, liquid barriers and other elements arranged in various configurations to manipulate the flow of a fluid sample in order to prepare such sample for analysis. Analysis of the sample may then be performed by any means known in the art. For example, as disclosed herein, microfluidic devices of the present invention may be used to facilitate the reaction of a blood sample with one or more reagents as part of a blood typing assay.

In one embodiment, a microfluidic device for analyzing a liquid sample is provided that comprises (a) a microfluidic channel having a first end and a second end, (b) a sample inlet fluidly connected to the first end of the microfluidic channel for receiving the liquid sample, (c) a filter interposed between the sample inlet and the first end of the microfluidic channel, wherein the filter removes selected particles from the liquid sample, (d) a bellows pump fluidly connected to the second end of the microfluidic channel, and (e) a liquid barrier interposed between the bellows pump and the second end of the microfluidic channel, wherein the liquid barrier is gas permeable and liquid impermeable.

In further embodiments, the bellows may comprise a vent hole, the filter may comprise a membrane, or the microfluidic device may further comprise (a) a first check valve interposed between the bellows pump and the liquid barrier, wherein the first check valve permits fluid flow towards the bellows pump, and (b) a second check valve fluidly connected to the bellows pump, wherein the second check valve permits fluid flow away from the bellows pump.

In another embodiment, a microfluidic device for analyzing a liquid sample is provided that comprises (a) a first microfluidic channel having a first end and a second end, (b) a sample inlet fluidly connected to the first end of the first microfluidic channel for receiving the liquid sample, (c) an active valve interposed between the sample inlet and the first end of the first microfluidic channel, (d) a means for actuating the active valve, (e) a first bellows pump fluidly connected to the second end of the first microfluidic channel, (f) a liquid barrier interposed between the first bellows pump and the second end of the first microfluidic channel, wherein the liquid barrier is gas permeable and liquid impermeable, (g) a second microfluidic channel having a first end and a second end, wherein the first end is fluidly connected to the first microfluidic channel at a location adjacent to the active valve, (h) a passive valve interposed between the first end of the second microfluidic channel and the first microfluidic channel, wherein the passive valve is open when the fluid pressure in the first microfluidic channel is greater than the fluid pressure in the second microfluidic channel, and (i) a sample reservoir fluidly connected to the second end of the second microfluidic channel.

In further embodiments, the first bellows pump may comprise a vent hole, the means for actuating the active valve may comprise a second bellows pump and/or the sample reservoir may comprise a vent hole.

In another embodiment, a microfluidic device for analyzing a liquid sample is provided that comprises (a) first and second microfluidic channels, each having a first end and a second end, (b) a sample inlet fluidly connected to the first end of the first microfluidic channel for receiving the liquid sample, (c) a first bellows pump fluidly connected to, and interposed between, the second end of the first microfluidic channel and the first end of the second microfluidic channel, (d) a second bellows pump fluidly connected to the second end of the second microfluidic channel, wherein the second bellows pump has a fluid outlet, (e) a first check valve interposed between the sample inlet and the first end of the first microfluidic channel, wherein the first check valve permits fluid flow towards the first microfluidic channel, (f) a second check valve interposed between the second end of the first microfluidic channel and the first bellows pump, wherein the second check valve permits fluid flow towards the first bellows pump, (g) a third check valve interposed between the first bellows pump and the first end of the second microfluidic channel, wherein the third check valve permits fluid flow towards the second microfluidic channel, and (h) a fourth check valve interposed between the second end of the second microfluidic channel and the second bellows pump, wherein the fourth check valve permits fluid flow towards the second bellows pump.

In another embodiment, a microfluidic device for analyzing a liquid sample is provided that comprises (a) a first microfluidic channel having a first end and a second end, (b) a sample inlet fluidly connected to the first end of the first microfluidic channel for receiving the liquid sample, (c) a first reagent inlet fluidly connected to the first end of the first microfluidic channel for receiving a first reagent, (d) a bellows pump fluidly connected to the second end of the first microfluidic channel, and (e) a first liquid barrier interposed between the bellows pump and the second end of the first microfluidic channel, wherein the liquid barrier is gas permeable and liquid impermeable.

In further embodiments, the bellows pump may comprise a vent hole or the microfluidic device may further comprise a check valve fluidly connected to the bellows pump, wherein the check valve permits fluid flow away from the bellows pump.

In another further embodiment, the microfluidic device further comprises (a) a second microfluidic channel having a first end, fluidly connected to the sample inlet, and a second end, fluidly connected to the bellows pump, (b) a second reagent inlet fluidly connected to the first end of the second microfluidic channel for receiving a second reagent, and (c) a second liquid barrier interposed between the bellows pump and the second end of the second microfluidic channel, wherein the second liquid barrier is gas permeable and liquid impermeable.

In yet another further embodiment, the microfluidic device further comprises (a) a third microfluidic channel having a first end, fluidly connected to the sample inlet, and a second end, fluidly connected to the bellows pump, (b) a third reagent inlet fluidly connected to the first end of the third microfluidic channel for receiving a third reagent, and (c) a third liquid barrier interposed between the bellows pump and the second end of the third microfluidic channel, wherein the third liquid barrier is gas permeable and liquid impermeable.

In one alternate embodiment of the foregoing, the first reagent inlet comprises a first blister pouch containing the first reagent, the second reagent inlet comprises a second blister pouch containing the second reagent, and the third reagent inlet comprises a third blister pouch containing the third reagent.

In another embodiment, a microfluidic device for analyzing a liquid sample is provided that comprises (a) a first microfluidic channel having a first end and a second end, (b) a sample inlet fluidly connected to the first end of the first microfluidic channel for receiving the liquid sample, (c) a first dried reagent zone, comprising a first reagent printed thereon, fluidly connected to the first end of the first microfluidic channel, (d) a bellows pump fluidly connected to the second end of the first microfluidic channel, and (e) a first liquid barrier interposed between the bellows pump and the second end of the first microfluidic channel, wherein the liquid barrier is gas permeable and liquid impermeable.

In further embodiments, the bellows pump may comprise a vent hole or the microfluidic device may further comprise a check valve fluidly connected to the bellows pump, wherein the check valve permits fluid flow away from the bellows pump.

In another further embodiment, the microfluidic device further comprises (a) a second microfluidic channel having a first end, fluidly connected to the sample inlet, and a second end, fluidly connected to the bellows pump, (b) a second dried reagent zone, comprising a second reagent printed thereon, fluidly connected to the first end of the second microfluidic channel, and (c) a second liquid barrier interposed between the bellows pump and the second end of the second microfluidic channel, wherein the second liquid barrier is gas permeable and liquid impermeable.

In yet another further embodiment, the microfluidic device further comprises (a) a third microfluidic channel having a first end, fluidly connected to the sample inlet, and a second end, fluidly connected to the bellows pump, (b) a third dried reagent zone, comprising a third reagent printed thereon, fluidly connected to the first end of the third microfluidic channel, and (c) a third liquid barrier interposed between the bellows pump and the second end of the third microfluidic channel, wherein the third liquid barrier is gas permeable and liquid impermeable.

In a more specific embodiment, the liquid sample comprises a blood sample, the first reagent comprises antibody-A, the second reagent comprises antibody-B, and the third reagent comprises antibody-D.

In yet a further embodiment, the microfluidic device further comprises a hydrating buffer inlet, fluidly connected to the first, second and third dried reagent zones and to the first ends of the first, second and third microfluidic channels, for receiving a hydrating buffer. In an alternate embodiment, the hydrating buffer inlet comprises a hydrating buffer blister pouch containing the hydrating buffer.

These and other aspects of the invention will be apparent upon reference to the attached figures and following detailed description.

DETAILED DESCRIPTION OF THE INVENTION

As noted previously, the present invention relates to microfluidic devices and methods utilizing a plurality of microfluidic channels, inlets, valves, membranes, pumps, liquid barriers and other elements arranged in various configurations to manipulate the flow of a fluid sample in order to prepare such sample for analysis and to analyze the fluid sample. In the following description, certain specific embodiments of the present devices and methods are set forth, however, persons skilled in the art will understand that the various embodiments and elements described below may be combined or modified without deviating from the spirit and scope of the invention.

Figure 1A:
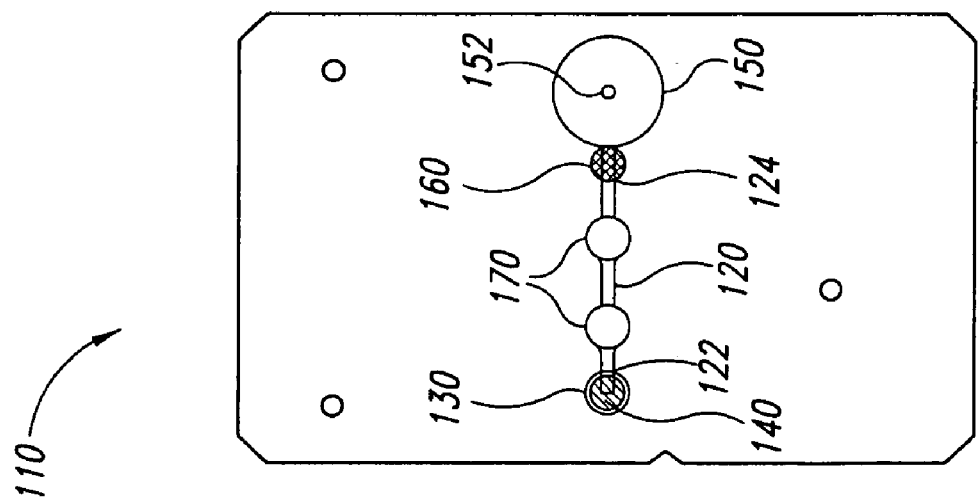
FIGS. 1A-1C are a series of cross-sectional views illustrating the operation of a first embodiment of a microfluidic device in accordance with aspects of the present invention.
Figure 1B:
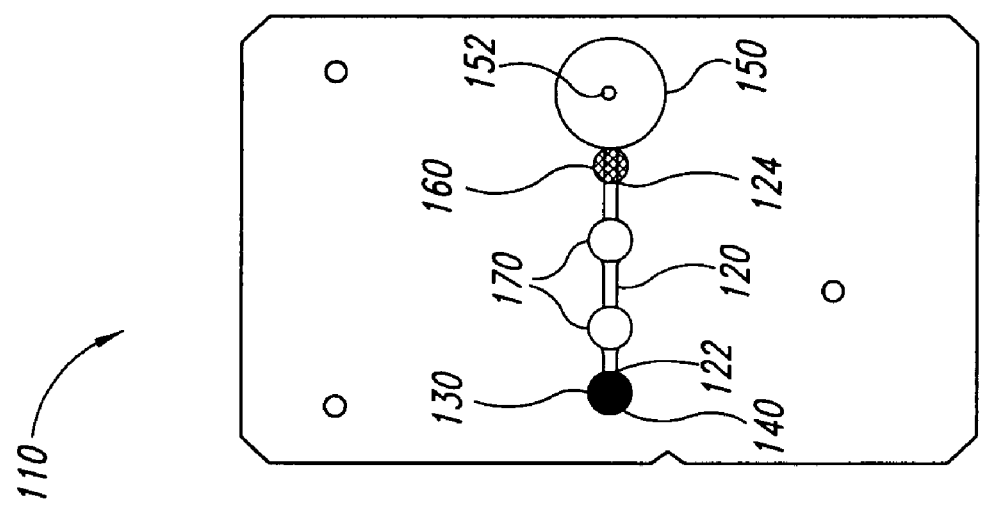
Figure 1C:
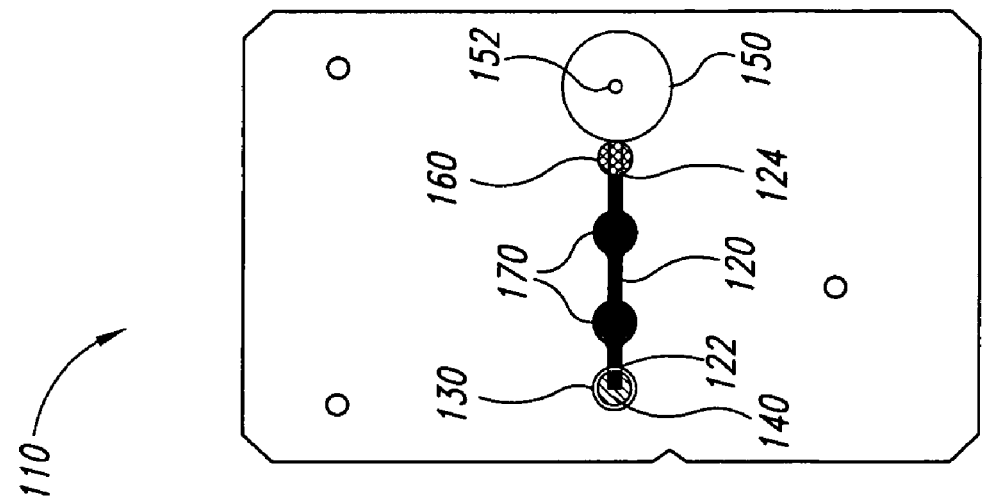

FIGS. 1A-1C are a series of cross-sectional views of the device 110 illustrating the operation of a first embodiment of the invention. As shown in FIG. 1A, microfluidic device 110 comprises a microfluidic channel 120 having a first end 122 and a second end 124. As illustrated, device 110 is in the form of a cartridge, however, the form of device 110 is not essential to the present invention, and persons of ordinary skill in the art can readily select a suitable form for a given application. The microfluidic devices of the present invention, such as device 110, may be constructed from a material, such as transparent plastic, mylar or latex, using a method such as injection molding or lamination.

As further shown in FIG. 1A, device 110 comprises a sample inlet 130 fluidly connected to first end 122 of microfluidic channel 120 for receiving a liquid sample and a filter 140 interposed between sample inlet 130 and first end 122 of microfluidic channel 120. Filter 140 is capable of removing selected particles, such as white blood cells, red blood cells, polymeric beads, such as polystyrene or latex with sizes from 1-100 microns, and bacteria cells, such as *E. coli*, from the liquid sample, and may comprise a membrane (as illustrated). A bellows pump 150 having a vent hole 152 is fluidly connected to second end 124 of microfluidic channel 120 and a liquid barrier 160 is interposed between bellows pump 150 and second end 124 of microfluidic channel 120. Liquid barrier 160 is a gas permeable and fluid impermeable membrane.

During operation, a liquid sample in placed into sample inlet 130 (as shown in FIG. 1B), bellows pump 150 is depressed, either manually by a user or mechanically by an external device, vent hole 152 is substantially sealed, such as by covering vent hole 152, and bellows pump 150 is then released. During depression of bellows pump 150, vent hole 152 remains uncovered so that fluid in bellows pump 150 may be expelled through vent hold 152. Upon release of bellows pump 150, a negative fluid pressure is created in microfluidic channel 120 and the liquid sample is drawn through filter 140 into, and through, microfluidic channel 120 to the liquid barrier 160 (as shown in FIG. 1C).

As further shown in FIG. 1A, microfluidic channel 120 may comprise one or more optical viewing area(s) 170. Optical viewing area(s) 170 enable visual verification by a user that the liquid sample is flowing through microfluidic channel 120.

Figure 2C:
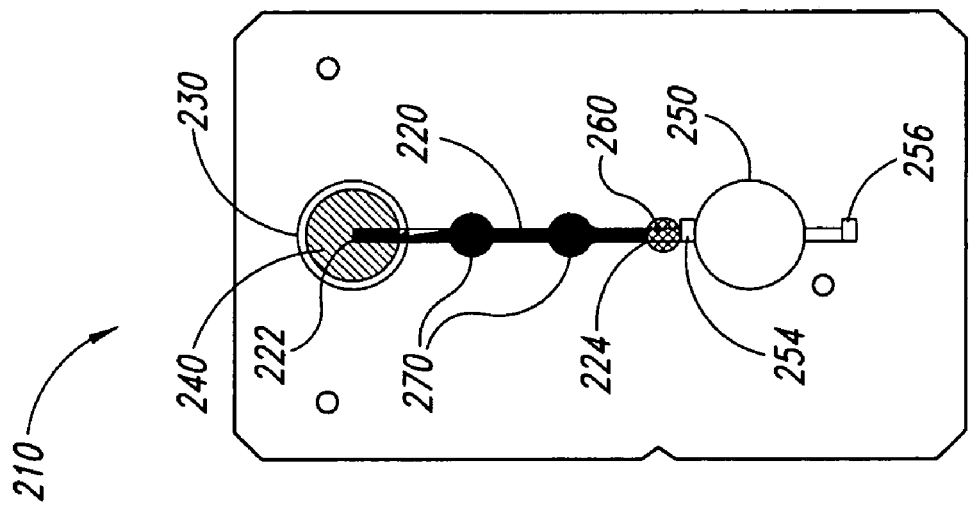
FIGS. 2A-2C are a series of cross-sectional views illustrating the operation of a second embodiment of a microfluidic device in accordance with aspects of the present invention.
Figure 2B:
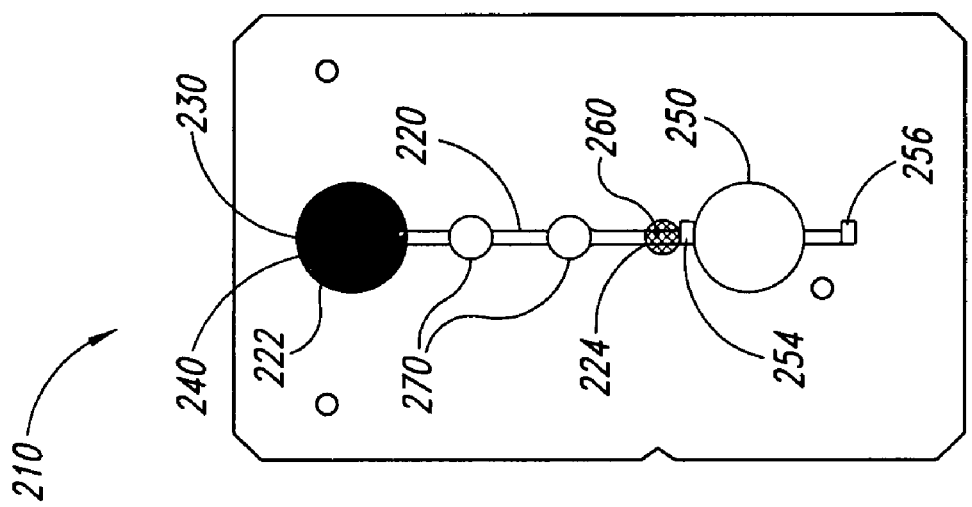
Figure 2A:
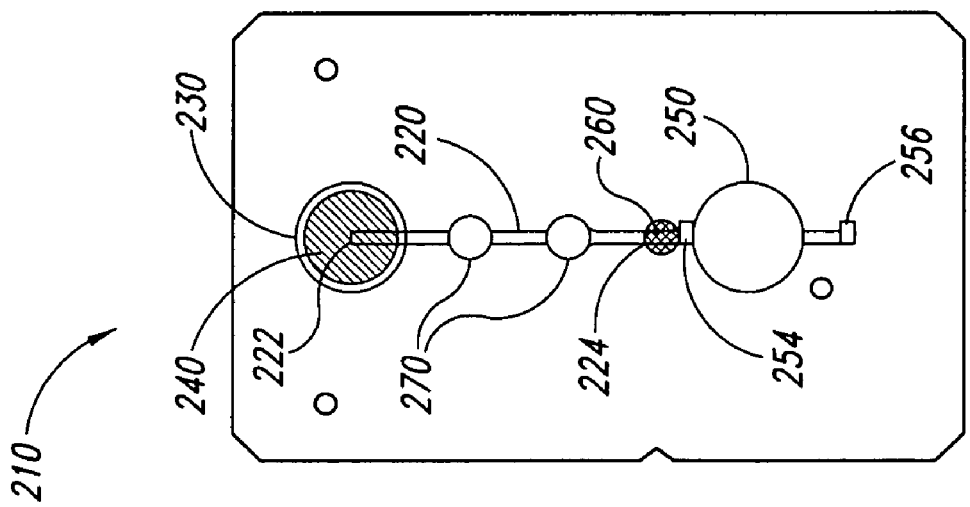

FIGS. 2A-2C are a series of cross-sectional views of the device 210 illustrating the operation of a second embodiment of the invention. Microfluidic device 210 illustrated in FIG. 2A is similar to device 110 of FIG. 1A and comprises a microfluidic channel 220 having a first end 222 and a second end 224, a sample inlet 230 fluidly connected to first end 222 of microfluidic channel 220 for receiving a liquid sample, a filter 240 interposed between sample inlet 230 and first end 222 of microfluidic channel 220, a bellows pump 250 fluidly connected to second end 224 of microfluidic channel 220 and a liquid barrier 260 interposed between bellows pump 250 and second end 224 of microfluidic channel 220.

Rather than providing a vent hole in bellows pump 250 as in FIG. 1A, device 210 utilizes first and a second check valves, 254 and 256, respectively, to prevent the fluid in bellows pump 250 from being expelled into microfluidic channel 220 during depression of bellows pump 250. Check valves, also known as one-way valves, permit fluid flow in one direction only. Exemplary check valves for use in microfluidic structures are described in U.S. Pat. No. 6,431,212, which is hereby incorporated by reference in its entirety. First check valve 254 is interposed between bellows pump 250 and liquid barrier 224 and permits fluid flow towards bellows pump 250. Second check valve 256 is fluidly connected to bellows pump 250 and permits fluid flow away from the bellows pump (for example, by venting to the atmosphere).

During operation, a liquid sample is placed into sample inlet 230 (as shown in FIG. 2B), bellows pump 250 is depressed, either manually by a user or mechanically by an external device, and, then, bellows pump 250 is released. During depression of bellows pump 250, first check valve 254 remains closed and prevents fluid flow from bellows chamber 250 into microfluidic channel 220; second check valve 256 opens and expels the fluid displaced from bellows pump 250. Upon release of bellows pump 250, a negative fluid pressure is created, first check valve 254 opens and permits fluid flow from microfluidic channel 220 into bellows pump 250, second check valve 256 closes and prevents fluid flow into bellows pump 250 from, for example, the atmosphere, and the liquid sample is drawn through filter 240 into, and through, microfluidic channel 220 to liquid barrier 260 (as shown in FIG. 2C).

In addition, similar to FIG. 1A, microfluidic channel 220 may optionally comprise one or more optical viewing area(s)

270 to enable visual verification by a user that the liquid sample is flowing through microfluidic channel 220.

Figure 3C:
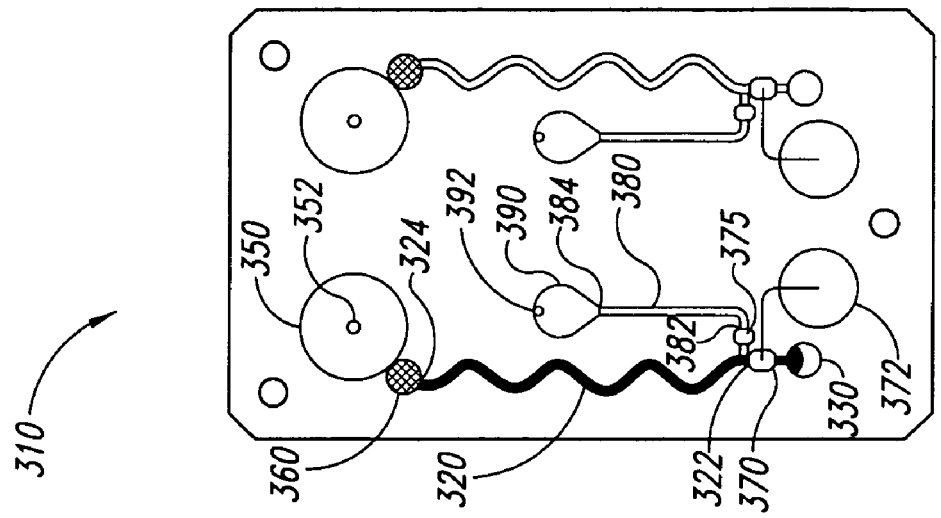
FIGS. 3A-3F are a series of cross-sectional views illustrating the operation of a third embodiment of a microfluidic device in accordance with aspects of the present invention.
Figure 3B:
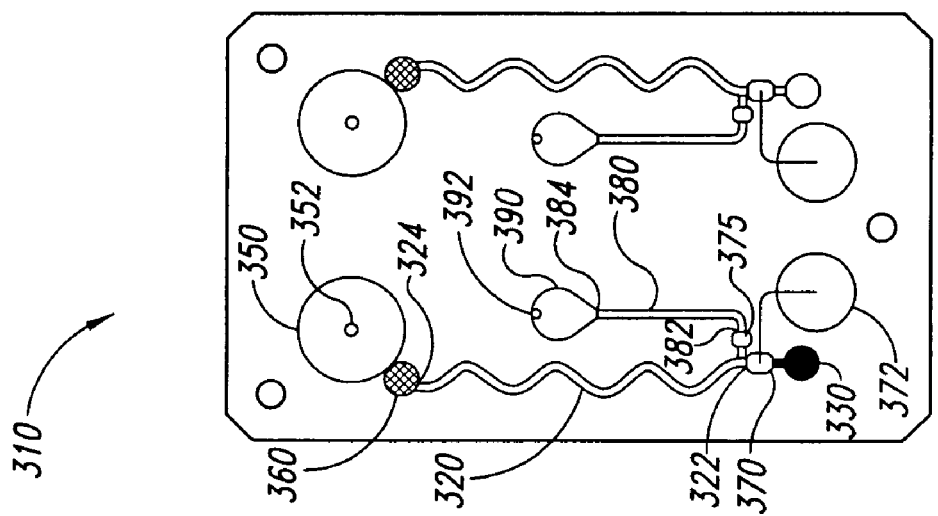
Figure 3A:
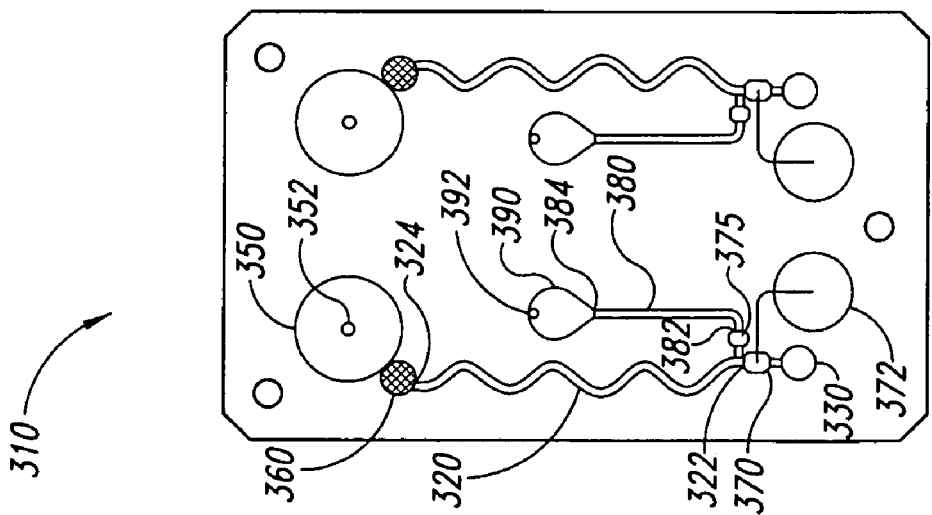
Figure 3F:
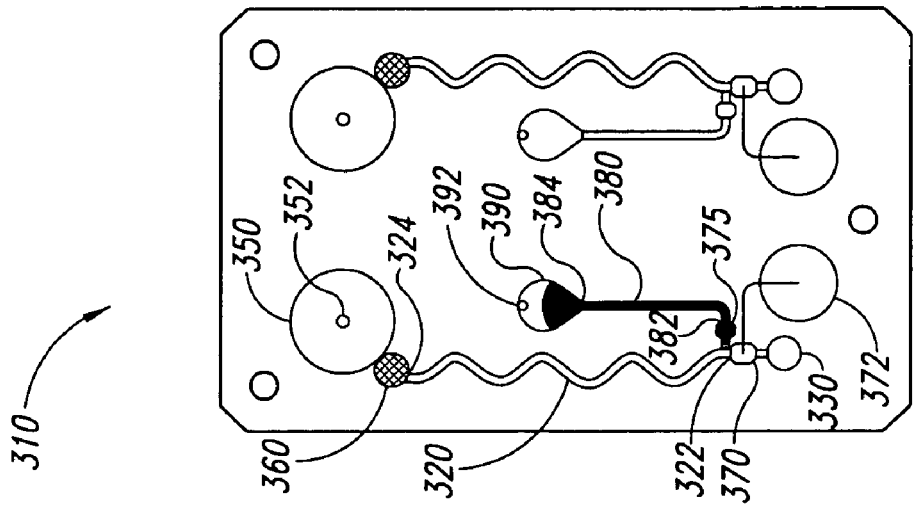
Figure 3E:
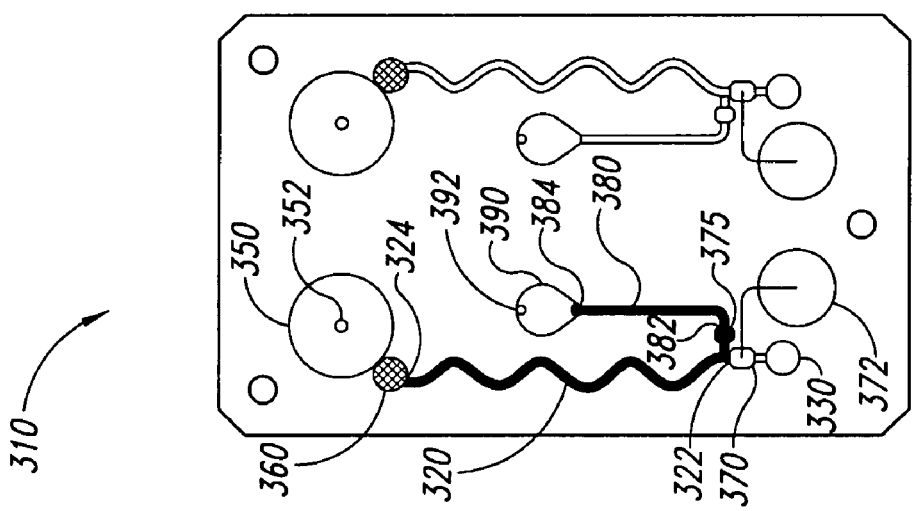

FIGS. 3A-3F are a series of cross-sectional views illustrating the operation of a third embodiment of the present invention. As shown in FIG. 3A, microfluidic device 310 comprises a first microfluidic channel 320 having a first end 322 and a second end 324. A sample inlet 330 is fluidly connected to first end 322 of first microfluidic channel 320 for receiving a liquid sample. A first bellows pump 350, having a vent hole 352, is fluidly connected to second end 324 of first microfluidic channel 320. Liquid barrier 360 is interposed between first bellows pump 350 and second end 324 of microfluidic channel 320. As in FIGS. 1A and 2A, the liquid barrier 360 is a gas permeable and liquid impermeable membrane.

Furthermore, device 310 comprises an on/off active valve 370 interposed between sample inlet 330 and first end 322 of first microfluidic channel 320 and a means 372 for actuating active valve 370. As illustrated, means 372 comprise a second bellows pump 372, however, persons of ordinary skill in the art can readily select an alternative and suitable means for applying manual or fluidic pressure to actuate active valve 370. Device 310 also comprises a second microfluidic channel 380 having a first end 382 and a second end 384. As shown, first end 382 of second microfluidic channel 380 is fluidly connected to first microfluidic channel 320 at a location adjacent to active valve 370 and second end 384 of second microfluidic channel 380 is fluidly connected to a sample reservoir 390 having a vent hole 392. A passive valve 375 is interposed between first end 382 of second microfluidic channel 380 and first microfluidic channel 320. Passive valve 375 is designed to be open when the fluid pressure in first microfluidic channel 320 is greater than the fluid pressure in second microfluidic channel 380. Exemplary passive valves, also known as zero dead volume valves, for use in microfluidic structures are described in U.S. patent application Ser. No. 10/114,890, which application is assigned to the assignee of the present invention and is hereby incorporated by reference in its entirety.

During initial operation, a liquid sample is placed into sample inlet 330 (as shown in FIG. 3B), first bellows pump 350 is depressed, either manually by a user or mechanically by an external device, vent hole 352 is covered and, then, first bellows pump 350 is released. During depression of first bellows pump 350, vent hole 352 remains uncovered so that fluid in first bellows pump 350 may be expelled through vent hold 352. Upon release of first bellows pump 350, a negative fluid pressure is created in microfluidic channel 320 and the liquid sample is drawn through active valve 370 and into, and through, microfluidic channel 320 to liquid barrier 360 (as shown in FIG. 3C). During this initial depression and release of first bellows pump 350, the fluid pressure in first microfluidic channel 320 is less than the fluid pressure in second microfluidic channel 380, thus passive valve 375 is closed and the liquid sample is prevented from flowing into second microfluidic channel 380.

Figure 3D:
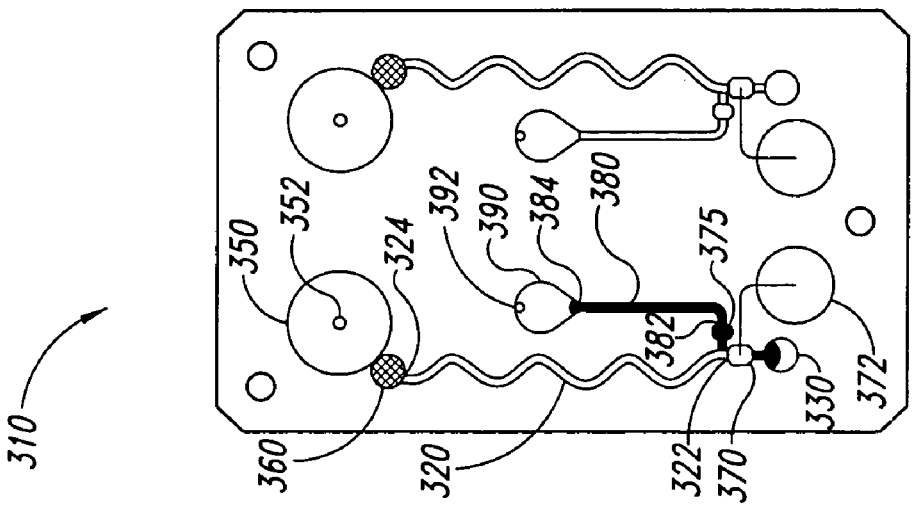

During the next stage of operation, shown in FIG. 3D, vent hole 352 is covered, second bellows pump 372 is depressed, thereby actuating (i.e., closing) active valve 370, and, then, first bellows pump 350 is depressed, thereby creating a positive fluid pressure in first microfluidic channel 320. As a result, the fluid pressure in first microfluidic channel 320 rises above (i.e., is greater than) the fluid pressure in second microfluidic channel 380, passive valve 375 opens, and the liquid sample is pushed from first microfluidic channel 320 into second microfluidic channel 380.

During an additional stage of operation, the foregoing two steps are repeated to draw an additional portion of the liquid sample into first microfluidic channel 320, and, then, push the additional portion of the liquid sample into second microfluidic channel 380, thereby pushing the first portion of the liquid sample already in second microfluidic channel 380 into sample reservoir 390. Depending on the amount of liquid sample and the size of sample reservoir 390, the foregoing additional stage of operation may be repeated a number of times.

As further shown in FIGS. 3A-3F, more than one of the microfluidic channel, pump and valve assemblies of the present invention may be disposed in a single microfluidic device. In this way, a number of fluid manipulations and analysis may be performed contemporaneously.

Figure 4A:
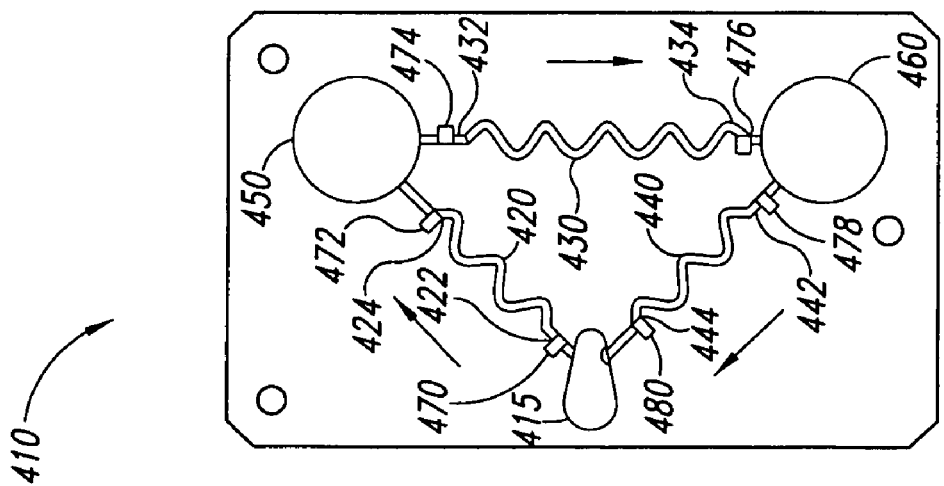
FIGS. 4A-4E are a series of cross-sectional views illustrating the operation of a fourth embodiment of a microfluidic device in accordance with aspects of the present invention.

FIGS. 4A-4E are a series of cross-sectional views illustrating the operation of a fourth embodiment of the invention. As shown in FIG. 4A, microfluidic device 410 comprises a first microfluidic channel 420 having a first end 422 and a second end 424, a second microfluidic channel 430 having a first end 432 and a second end 434, and a third microfluidic channel 440 having a first end 442 and a second end 444. A sample inlet 415, for receiving a liquid sample, is fluidly connected to, both, first end 422 of first microfluidic channel 420 and second end 444 of third microfluidic channel 440. A first bellows pump 450 is fluidly connected to, and interposed between, second end 424 of first microfluidic channel 420 and first end 432 of second microfluidic channel 430 and a second bellows pump 460 is fluidly connected to, and interposed between, second end 434 of second microfluidic channel 430 and first end 442 of third microfluidic channel 440.

As shown, device 410 also comprises a plurality of check valves. A first check valve 470 is interposed between sample inlet 415 and first end 422 of first microfluidic channel 420, and permits fluid flow towards first microfluidic channel 420. A second check valve 472 is interposed between second end 424 of first microfluidic channel 420 and first bellows pump 450, and permits fluid flow towards first bellows pump 450. A third check valve 474 is interposed between first bellows pump 450 and first end 432 of second microfluidic channel 430, and permits fluid flow towards second microfluidic channel 430. A fourth check valve 476 is interposed between second end 434 of second microfluidic channel 430 and second bellows pump 460, and permits fluid flow towards second bellows pump 460. A fifth check valve 478 is interposed between second bellows pump 460 and first end 442 of third microfluidic channel 440, and permits fluid flow towards third microfluidic channel 440. A sixth check valve 480 is interposed between second end 444 of third microfluidic channel 440 and sample inlet 415, and permits fluid flow towards sample inlet 415. As in FIG. 2A, first, second, third, fourth, fifth and sixth check valves, 470, 472, 474, 476, 478 and 480, permit fluid flow in one direction only (as noted by the arrows in FIG. 4A). As noted before, exemplary check valves for use in microfluidic structures are described in U.S. Pat. No. 6,431,212.

Figure 4B:
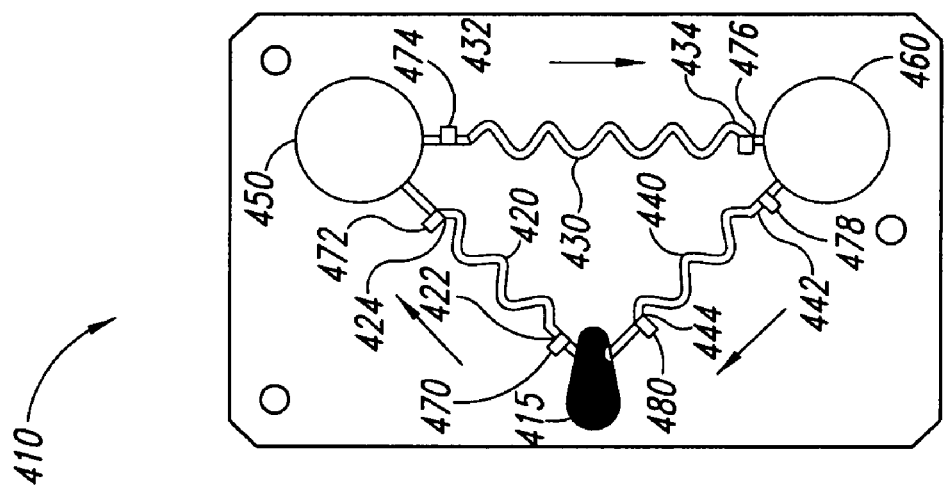
Figure 4C:
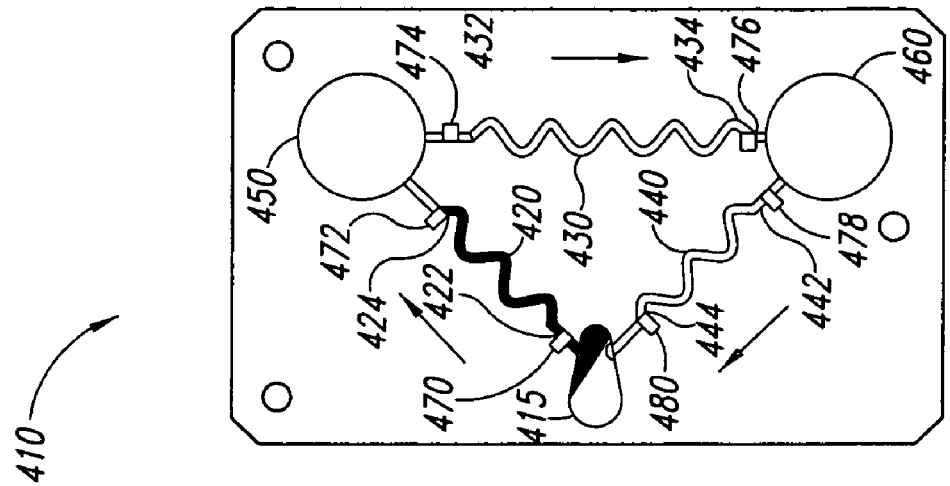
Figure 4E:
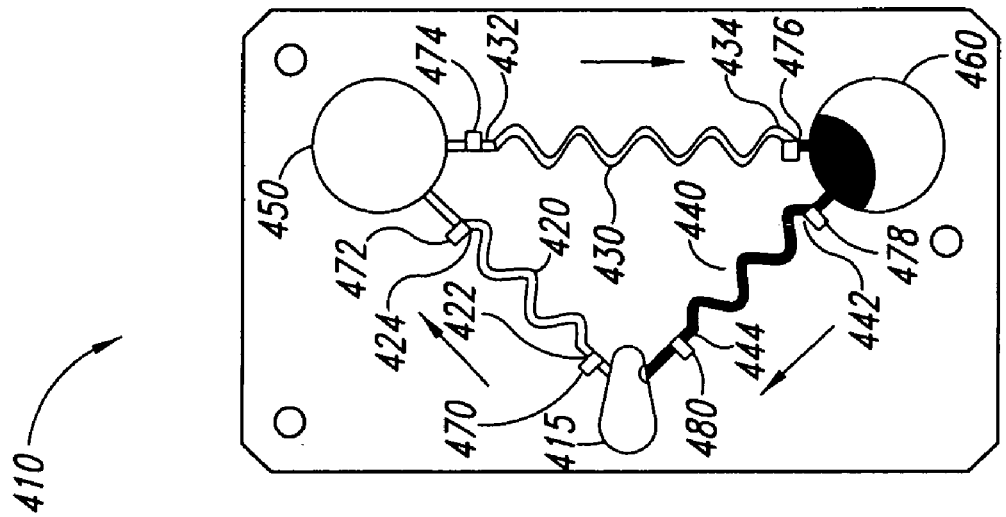
Figure 4D:
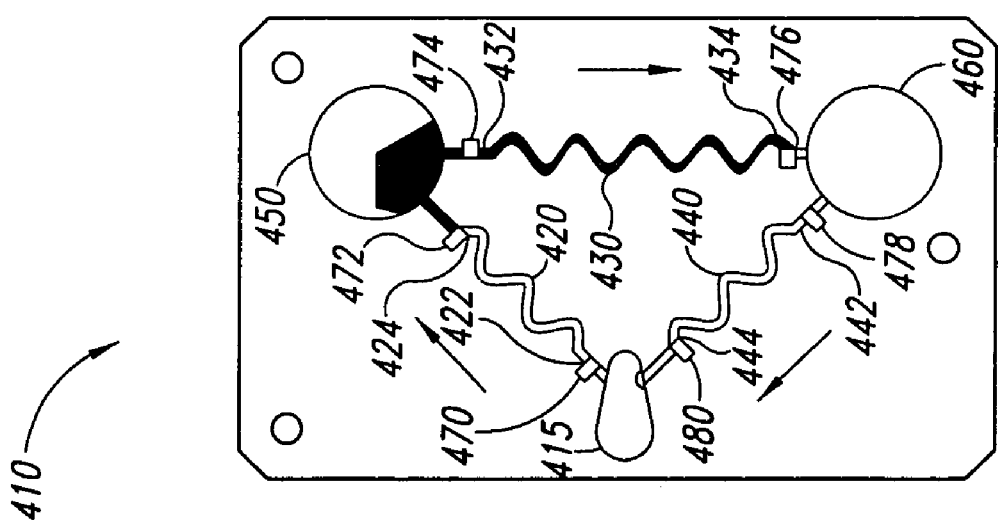

During operation, a liquid sample in placed into sample inlet 415 (as shown in FIG. 4B) and first and second bellows pumps 450 and 460 are alternately, sequentially and/or repeatedly depressed and released, either manually by a user or mechanically by an external device, to draw and push the liquid sample through first, second and third microfluidic channels 420, 430 and 440 (as shown in FIGS. 4C through 4E). During these series of depressions and releases, first, second, third, fourth, fifth and sixth check valves, 470, 472, 474, 476, 478 and 480, ensure that the liquid sample flows in one continuous direction through microfluidic device 410.

In variations of this fourth embodiment, rather than being fluidly connected to a third microfluidic channel 440, which is fluidly connected to sample inlet 415 to form a fluidic loop, one or more fluid outlet(s) of second bellows pump 460 may be fluidly connected to one or more microfluidic channel(s), which are, in turn, fluidly connected to one or more additional microfluidic channel(s), bellows pumps and check valves. In this way, a person of ordinary skill in the art will appreciate that a series of check valves and bellows pumps may be assembled and utilized in a multitude of different configurations to move a liquid sample through a network of microfluidic channels.

Figure 5C:
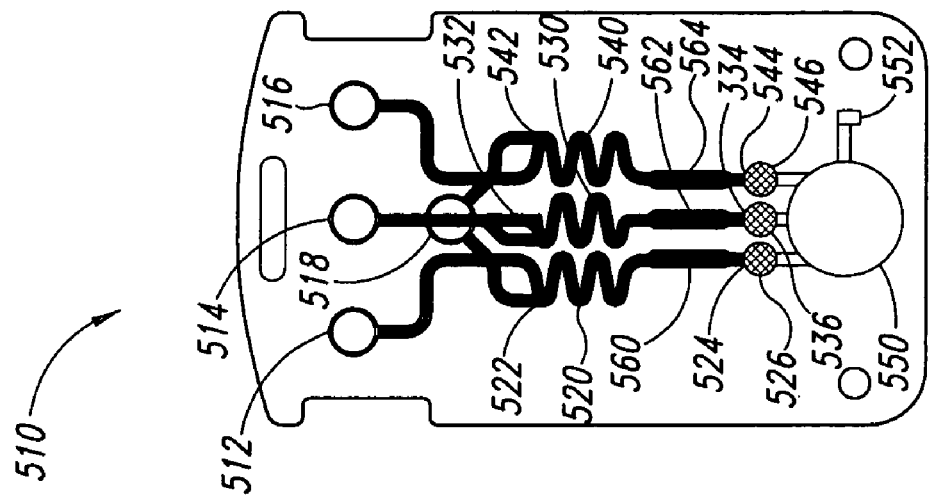
FIGS. 5A-5C are a series of cross-sectional views illustrating the operation of a fifth embodiment of a microfluidic device in accordance with aspects of the present invention.
Figure 5B:
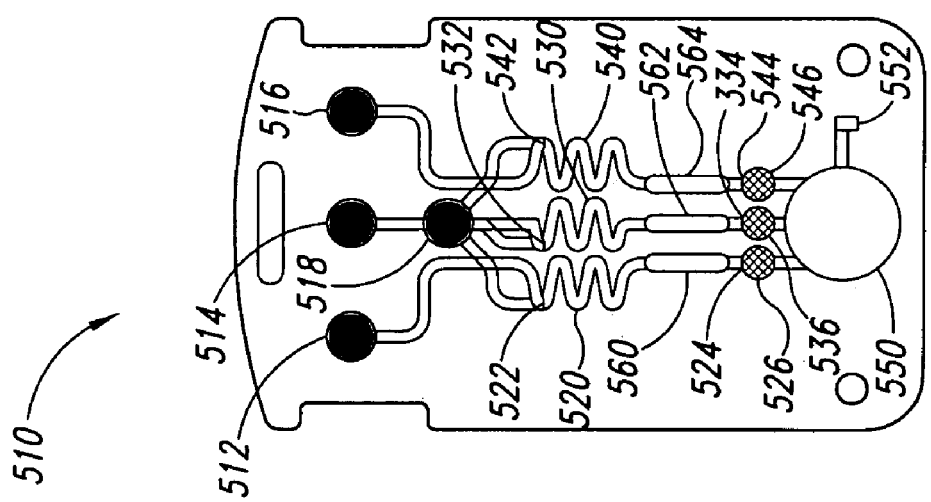
Figure 5A:
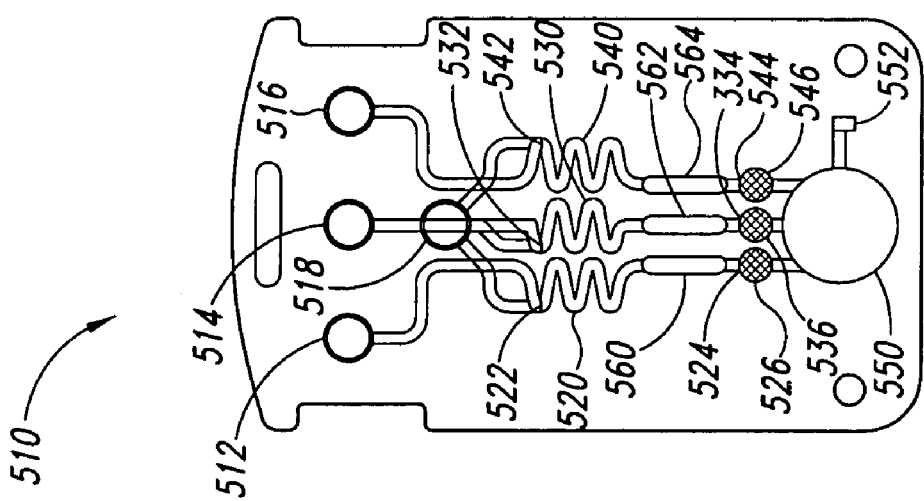

FIGS. 5A-5C are a series of cross-sectional views of a microfluidic device 510 illustrating the operation of a fifth embodiment of the invention. Microfluidic device 510 illustrated in FIG. 5A comprises a first microfluidic channel 520 having a first end 522 and a second end 524, a second microfluidic channel 530 having a first end 532 and a second end 534, and a third microfluidic channel 540 having a first end 542 and a second end 544. Sample inlet 518 is fluidly connected to first ends 522, 532 and 542 of first, second and third microfluidic channels 520, 530 and 540.

Device 510 further comprises a first reagent inlet 512 for receiving a first reagent, a second reagent inlet 514 for receiving a second reagent and a third reagent inlet 516 for receiving a third reagent. In alternate embodiments, the first, second and third reagents may be loaded during the manufacture of device 510 and first, second and third reagent inlets 512, 514 and 516 may comprise, for example, first, second and third blister pouches (not shown) containing the first, second and third reagents. Such blister pouches are adapted to burst, or otherwise release the first, second and third reagents into device 510, upon actuation, such as, for example, depression of the blister pouches either manually by a user or mechanically by an external device.

As illustrated, each of the first, second and third reagent inlets 512, 514 and 516 are fluidly connected to first ends 522, 532 and 542 of first, second and third microfluidic channels 520, 530 and 540. Bellows pump 550 is fluidly connected to second ends 524, 534 and 544 of first, second and third microfluidic channels 520, 530 and 540, and first, second and third liquid barriers 526, 536 and 546 are interposed between bellows pump 550 and second ends 524, 534 and 544 of first, second and third microfluidic channels 520, 530 and 540. As in FIGS. 1A, 2A and 3A, first, second and third liquid barriers 526, 536 and 546 are gas permeable and liquid impermeable membranes.

As shown, bellows pump 550 is fluidly connected to a check valve 552, which permits fluid flow away from bellows pump 550. Alternatively, the bellows pump may comprise a vent hole as in the embodiments of FIG. 1A and 3A.

During operation, a liquid sample in placed into sample inlet 518, a first reagent in placed into first reagent inlet 512, a second reagent is placed into second reagent inlet 514 and a third reagent is placed third reagent inlet 516 as shown in FIG. 5B. (In the alternate embodiment, wherein first, second and third reagent inlets 512, 514 and 516 comprise blister pouches containing the first, second and third reagents, operation is commenced by placing a liquid sample into sample inlet 518 and manually actuating the blister pouches to release the first, second and third reagents). Bellows pump 550 is then depressed, either manually by a user or mechanically by an external device, and, then, bellows pump 550 is released. During depression of bellows pump 550, check valve 552, or a vent hole (not shown), prevents fluid flow from bellows pump 550 into first, second and third microfluidic channels 520, 530 and 540. Upon release of bellows pump 550, a negative fluid pressure is created in first, second and third microfluidic channels 520, 530 and 540 and the liquid sample, the first reagent, the second reagent and the third reagent are drawn into, and through, first, second and third microfluidic channels 520, 530 and 540 to first, second and third liquid barriers 526, 536 and 546 (as shown in FIG. 5C). During this process, mixing of the liquid sample and the first, second and third reagents occurs within first, second and third microfluidic channels 520, 530 and 540.

In addition, similar to FIGS. 1A and 2A, first, second and third microfluidic channels 520, 530 and 540 may comprise one or more optical viewing areas 560, 562 and 564 to enable visual verification that the liquid sample and the first, second and third reagents are flowing through first, second and third microfluidic channels 520, 530 and 540. In addition, optical viewing areas 560, 562 and 564 enable a user to visually observe reactions occurring between the liquid same and the first, second and third reagents.

Microfluidic device 510 may be used as a rapid, disposable, blood typing assay. Such an assay may be utilized, for example, to provide bedside confirmation of a patient's ABO group prior to a blood transfusion. FIGS. 6A-6F are schematic illustrations of blood typing cards in accordance with aspects of the present invention.

Figure 6A:
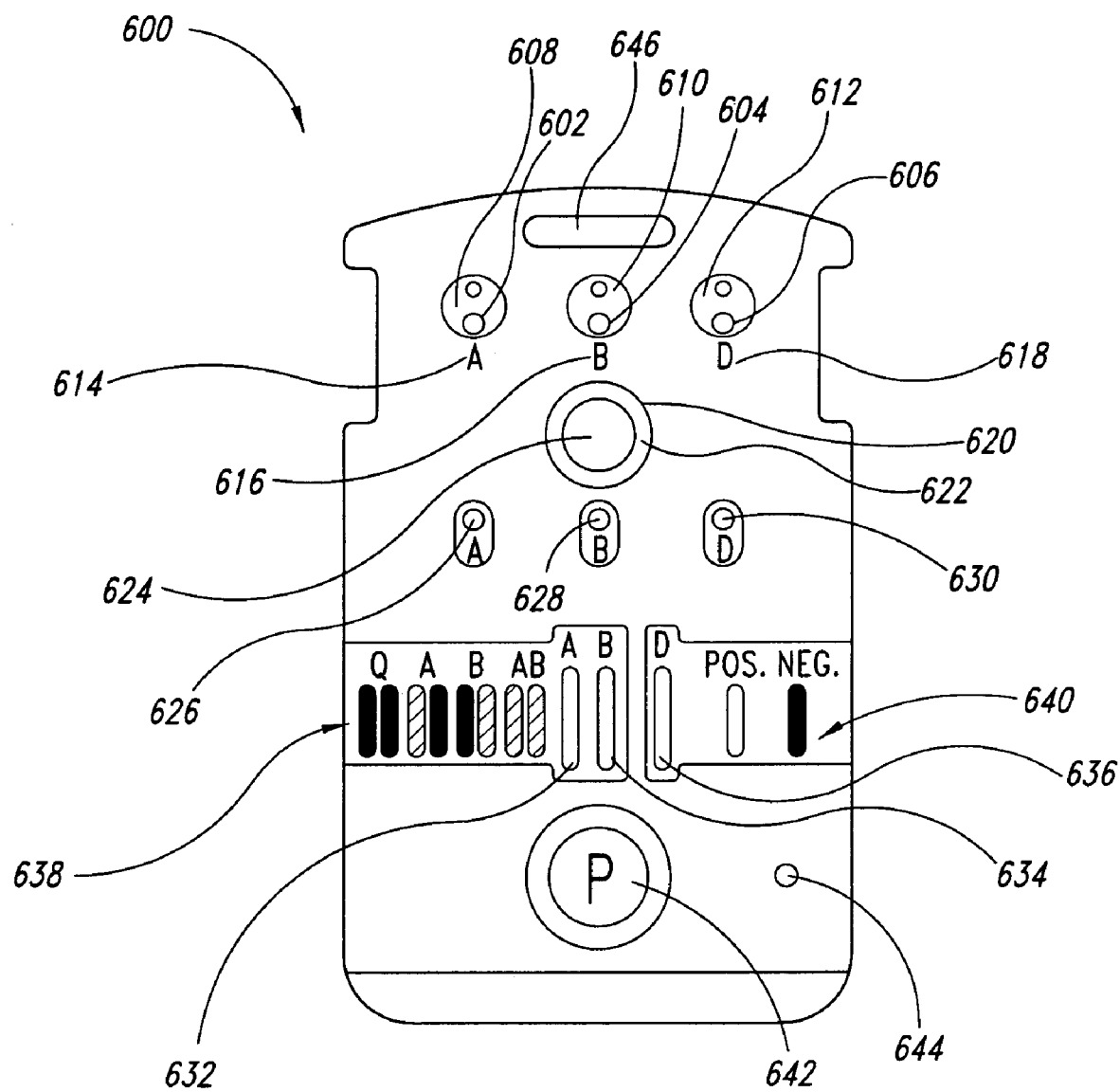
FIGS. 6A-6F are schematic illustrations of blood typing cards in accordance with aspects of the present invention.

FIG. 6A illustrates a microfluidic device, or a card, 600. In this embodiment reagent inlets for antibody-A 602, antibody-B 604, and antibody-D 606 are illustrated. Alternatively, as noted above with respect to FIGS. 5A-5C, such reagents may be loaded during the manufacture of device 600 and inlets 602, 604 and 606 may be eliminated by replacing such inlets with first, second and third blister pouches containing the reagents. For ease of use, inlets 602, 604 and 606, which provide access to filling the corresponding reservoirs 608, 610, and 612, respectively, are optionally marked with decorative indicators 614, 616, and 618.

FIG. 6A further shows a sample inlet 620 for accepting a blood sample or other fluid sample for testing. In the present embodiment sample 620 is labeled with a decorative indicator 622. The decorative indicator 622 encircles a transparent window 624 that provides a visual indicator of the reservoir for the fluid accepted through sample inlet 620. In alternative embodiments, window 624 may be omitted.

FIG. 6A further illustrates verification windows for the three reagents 626, 628 and 630. These verification windows are aligned over the corresponding microfluidic channels in order to provide visual verification that the reagents are in fact traveling through the microfluidic channels as designed. As with the reagent inlets, the reagent verification windows are appropriately marked.

FIG. 6A further illustrates appropriately marked optical viewing areas 632, 634 and 636 for viewing the blood typing results. In the current embodiment a legend 638 is provided to interpret the visual results and aid the user in determining the blood type. A further legend 640 is provided to aid the user in determining whether the blood is Rh positive or Rh negative.

FIG. 6A further shows a bellows pump 642 for actuating fluid flow through the device. The bellows pump is fluidly connected with an outlet port 644.

The embodiment in FIG. 6A further comprises an aperture 646 designed to accept an affixing device such that the microfluidic device may be attached directly to the container of fluid or bag of blood to be blood typed. In alternate embodiments, the affixing mechanism may include adhesive tape, a tie mechanism, a clamp, or may simply be inserted in a pocket on the fluid container, or any other standard means of affixing the device in position.

Figure 6B:
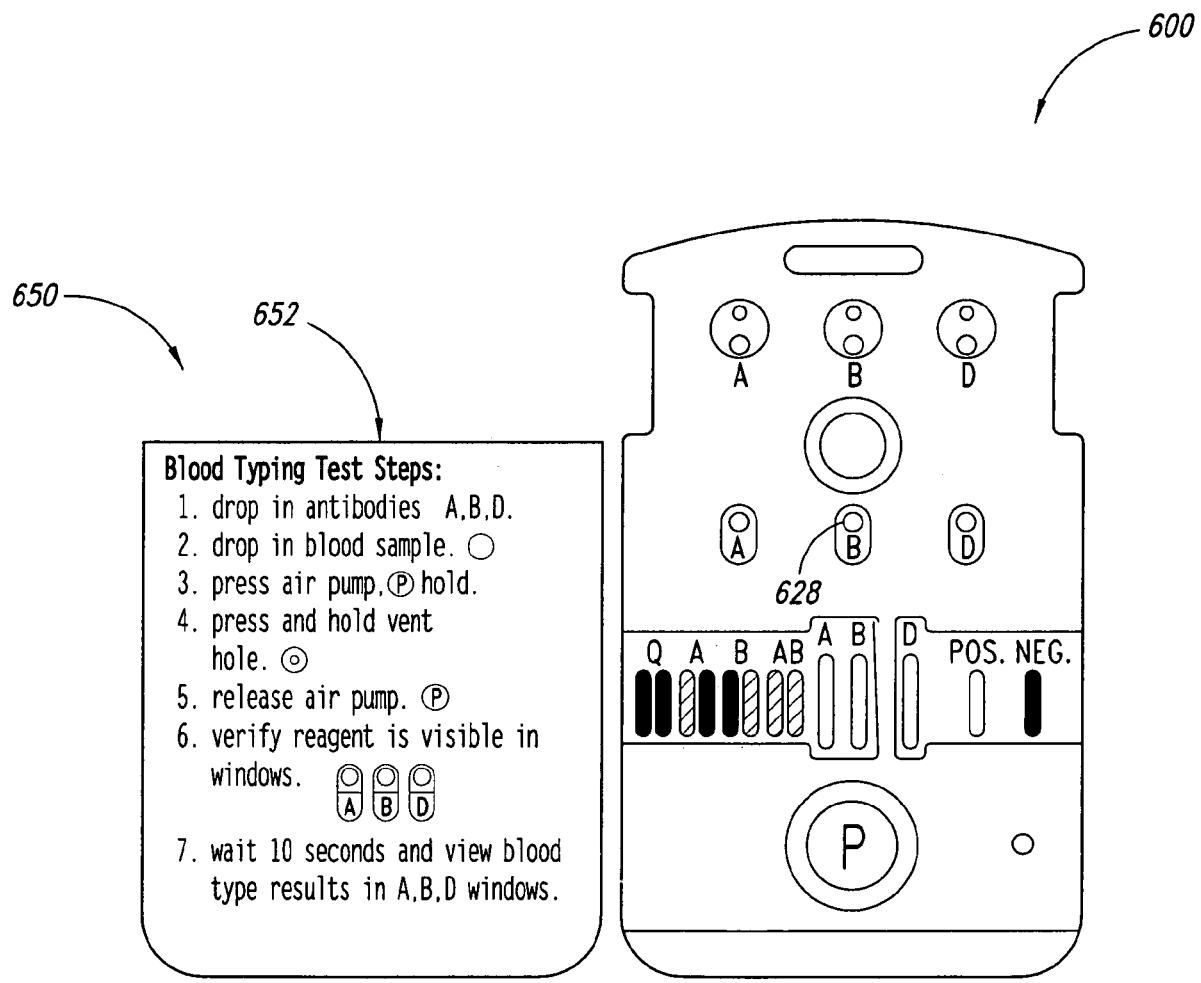

FIG. 6B illustrates an embodiment of microfluidic device 600 including a faceplate 650 attached to the device. FIG. 6B shows the inlets, verification windows, legends, and markings as shown in FIG. 6A, however, FIG. 6B further shows an open faceplate or cover plate 650 attached to device 600. In the illustrated embodiment, faceplate 650 is hingedly connected to the device 600. In alternate embodiments, the faceplate may be detached. When faceplate 650 is in an open position, the exposed side may further include operational instructions 652 for the convenience of the user. The faceplate additionally protects the viewing windows and inlets of the device when device 600 is not in use.

Figure 6C:
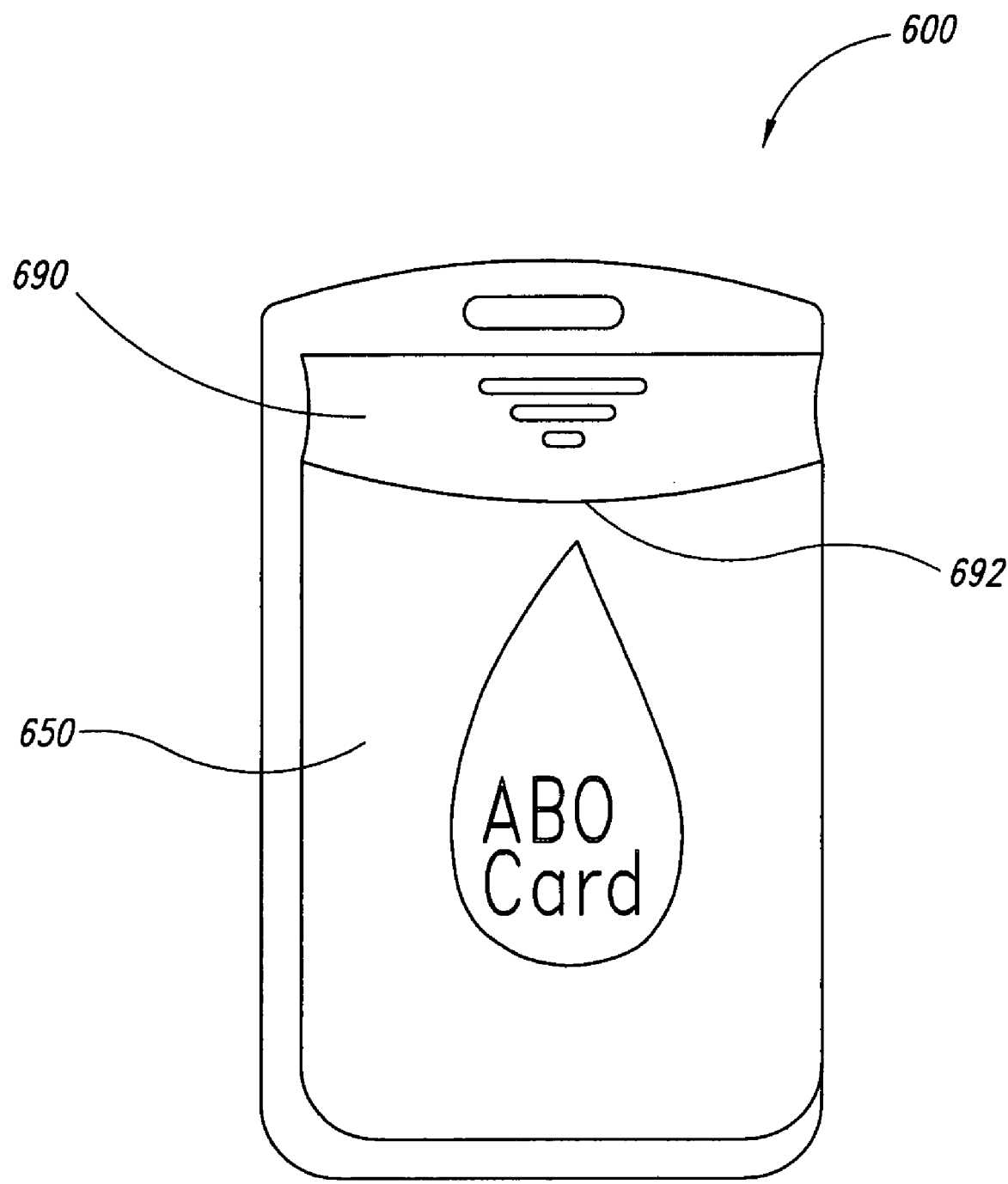
Figure 6D:
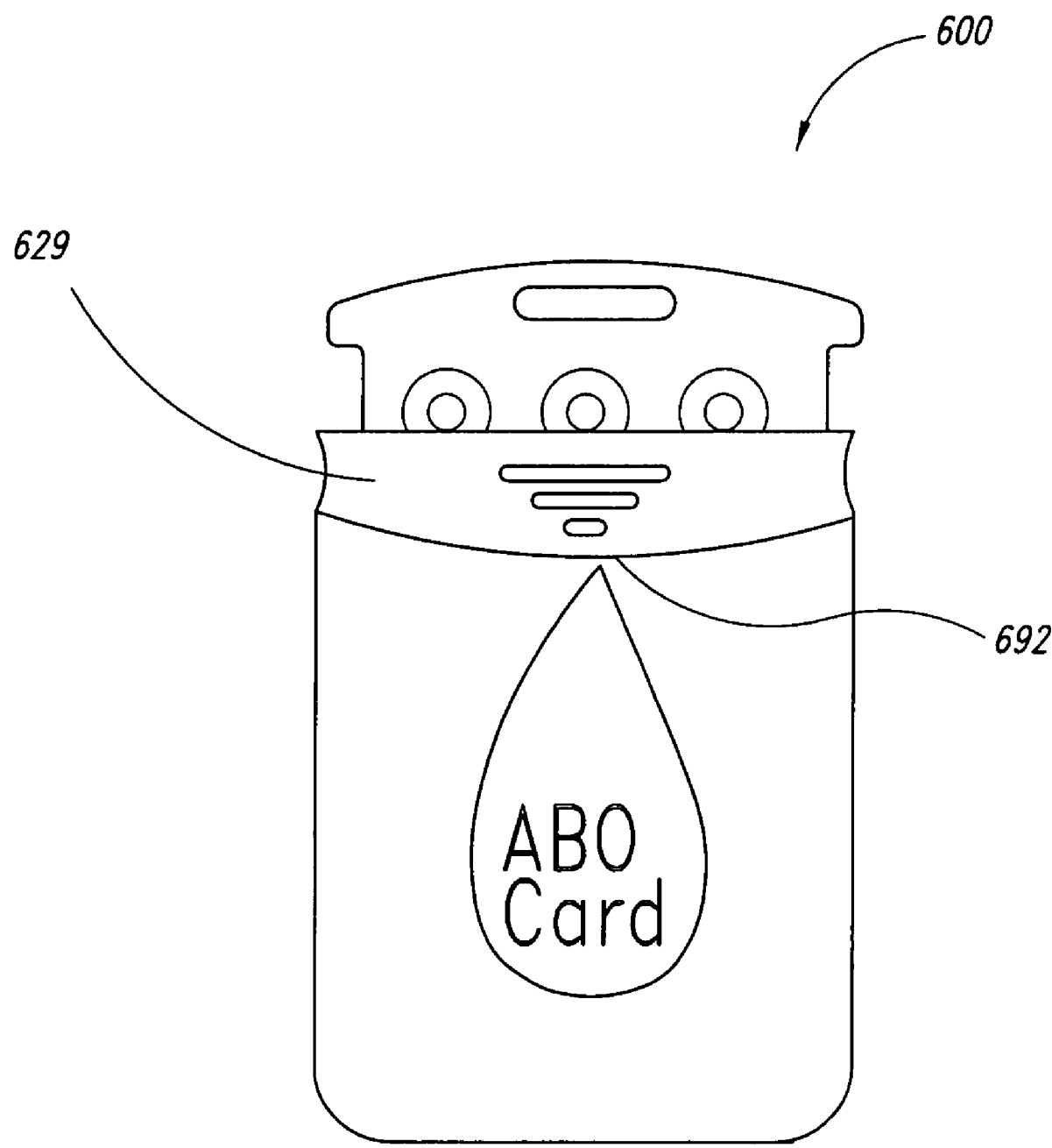

FIG. 6C illustrates yet another embodiment and shows microfluidic device 600 with a closed faceplate 650, covering the inlets, viewing windows, and legends shown in FIG. 6A, and a sheath 690. The sheath in the present embodiment is slideable and when slid in a downward direction, a lower lip 692 of the sheath provides a locking mechanism holding the faceplate in place. The faceplate 650, as noted previously, provides protection to the underlying inlets, viewing windows, legends, and legend drawings contained on the device. The faceplate 650 may additionally be used as a containment mechanism after the blood typing is complete, thus preventing contact with the blood or fluid being tested. FIG. 6D further illustrates the embodiment of FIG. 6C and shows the device when sheath 690 is slid into the locking position, thus holding faceplate 650 in the closed position.

Figure 6E:
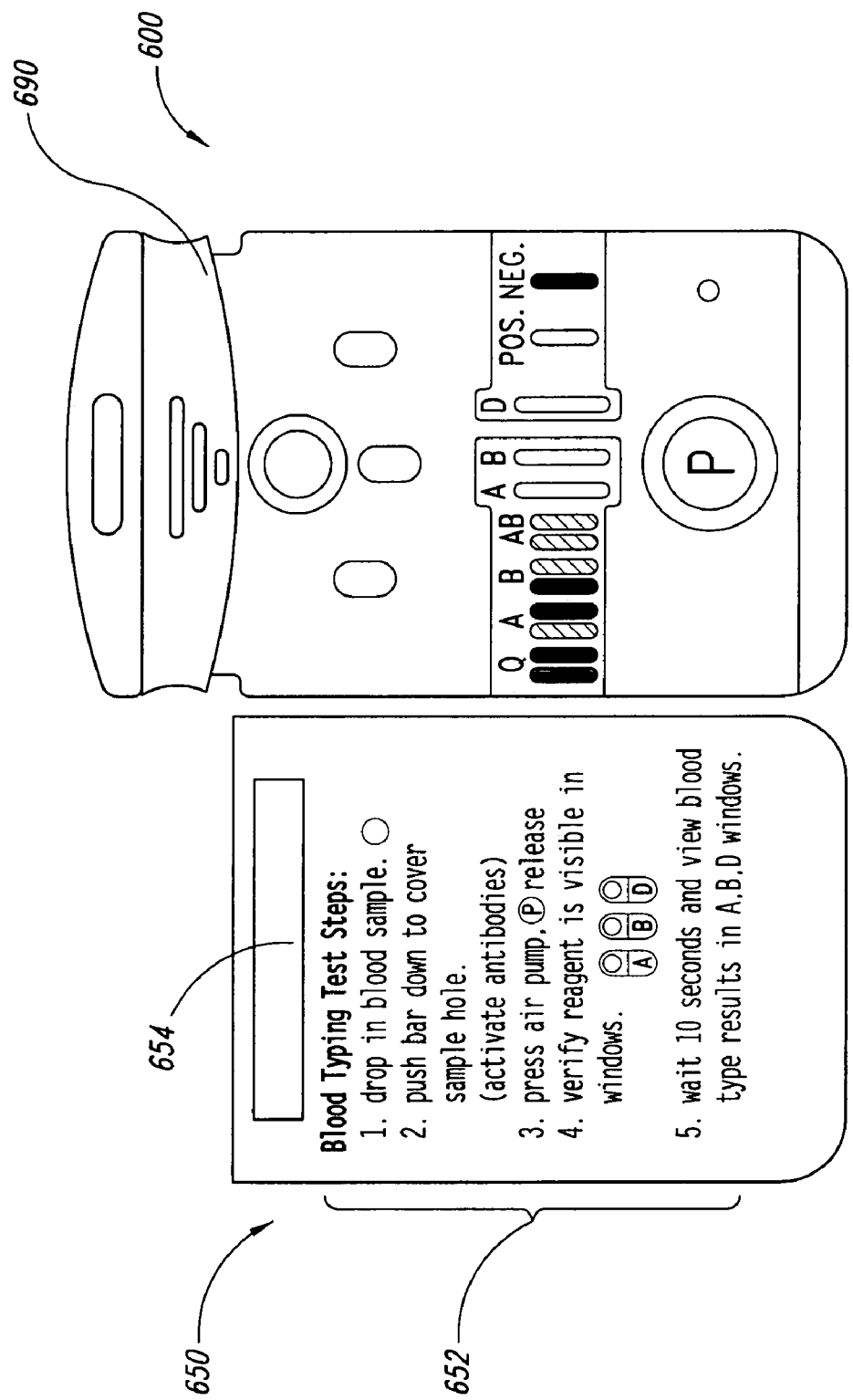

FIG. 6E illustrates another embodiment of the attached faceplate 650. In this embodiment the faceplate 650 includes operational instructions 652 for completing the blood typing test. The faceplate cover in this embodiment further includes an adhesive strip 654 that may be used to seal the sample inlet, or alternatively may be used to hold the faceplate closed. FIG. 6E further illustrates that the sheath 690 in this embodiment is covering the antigen reservoirs. In a further embodiment, downward movement of the sheath 690 may be utilized to actuate release of the antigens from the reservoirs.

Figure 6F:
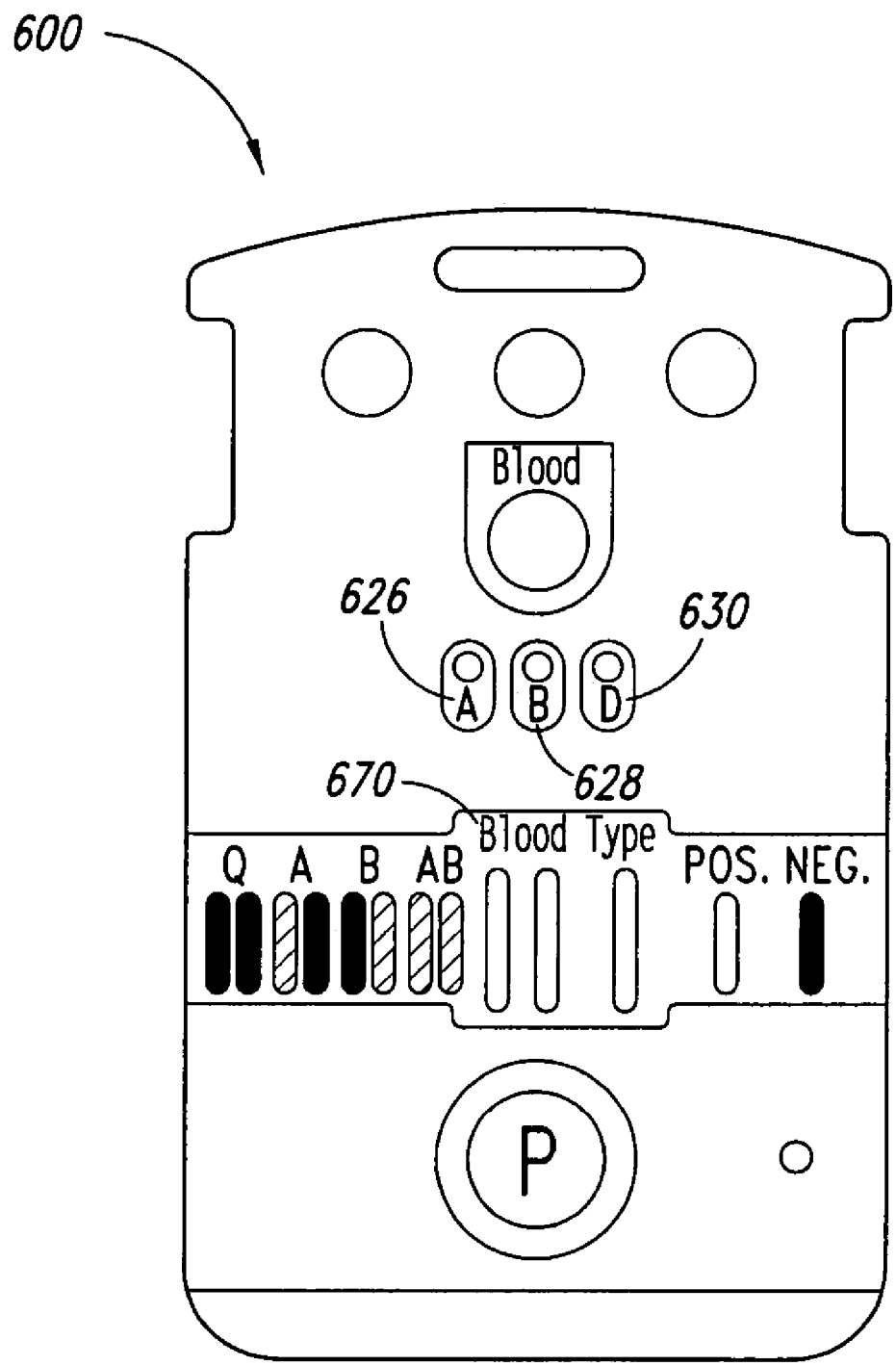

FIG. 6F shows an alternative configuration of device 600 and layout for user ease. In FIG. 6F, the reagent verification windows 626, 628 and 630 are grouped together for easier verification. Furthermore, in this embodiment, a header 670 is included identifying the blood type windows. Further use of the legends on alternative embodiments may include use of specific colors to delineate various functions on the substrate. For example, a red circle may encircle the blood port.

Figure 7A:
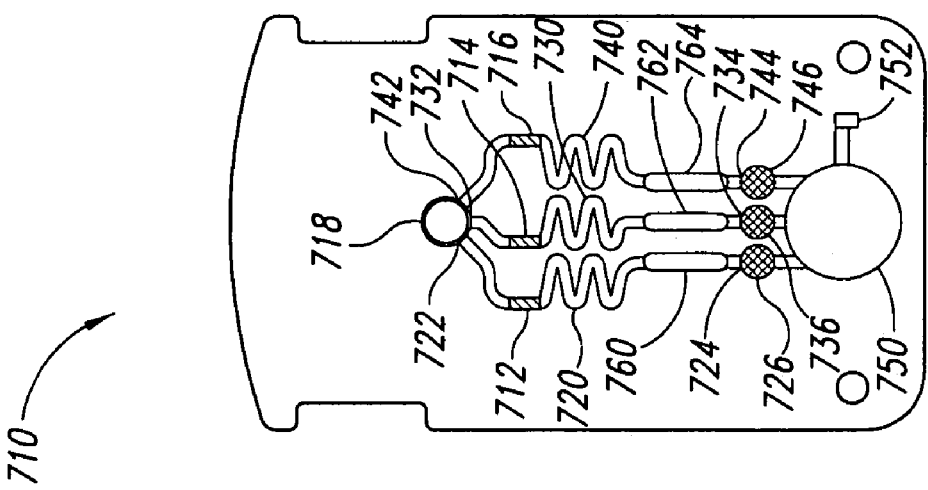
FIGS. 7A-7C are a series of cross-sectional views illustrating the operation of a sixth embodiment of a microfluidic device in accordance with aspects of the present invention.
Figure 7B:
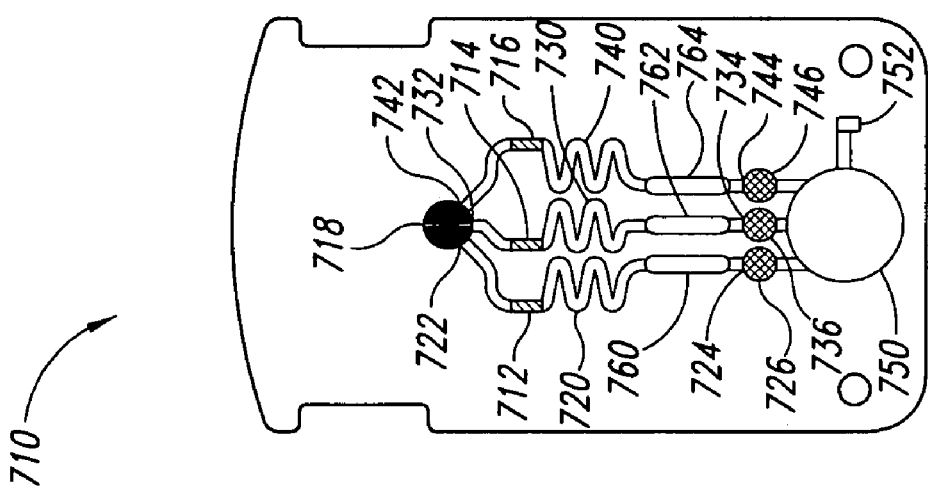
Figure 7C:
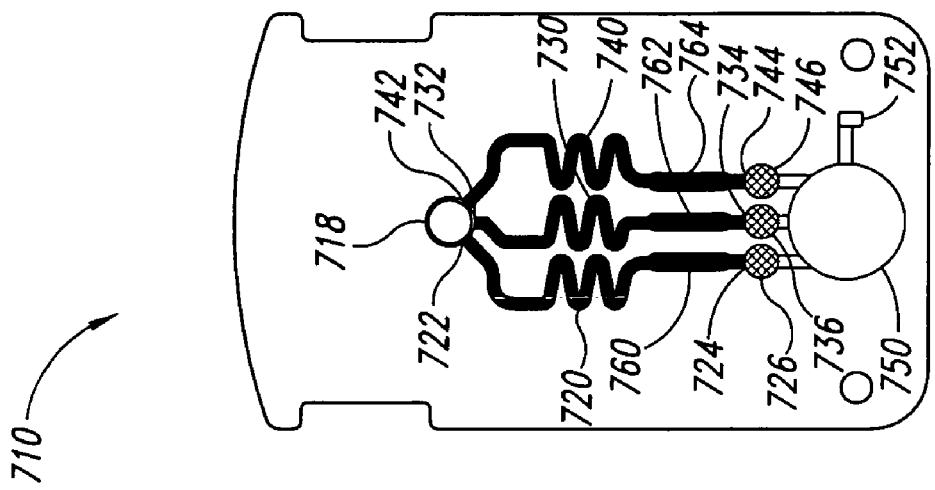

FIGS. 7A-7C are a series of cross-sectional views of a microfluidic device 710 illustrating the operation of a sixth embodiment of the invention. Microfluidic device 710 illustrated in FIG. 7A comprises a first microfluidic channel 720 having a first end 722 and a second end 724, a second microfluidic channel 730 having a first end 732 and a second end 734, and a third microfluidic channel 740 having a first end 742 and a second end 744. Sample inlet 718 is fluidly connected to first ends 722, 732 and 742 of first, second and third microfluidic channels 720, 730 and 740.

Rather than comprising first, second and third reagent inlets for receiving first, second and third reagents, similar to device 510 of FIGS. 5A-5C, first microfluidic channel 720 of device 710 comprises a first dried reagent zone 712 wherein a first reagent in printed, second microfluidic channel 730 of device 710 comprises a second dried reagent zone 714 wherein a second reagent is printed, and third microfluidic channel 740 comprises a third dried reagent zone 716 wherein a third reagent is printed. The first, second and third reagents may be printed onto first, second and third microfluidic channels 720, 730 and 740, respectively, during the manufacture of device 710 by methods such as ink jet printing, micro drop printing and transfer printing.

As illustrated, bellows pump 750 is fluidly connected to second ends 724, 734 and 744 of first, second and third microfluidic channels 720, 730 and 740, and first, second and third liquid barriers 726, 736 and 746 are interposed between bellows pump 750 and second ends 724, 734 and 744 of first, second and third microfluidic channels 720, 730 and 740. As in FIGS. 1A, 2A, 3A and 5A, first, second and third liquid barriers 726, 736 and 746 are gas permeable and liquid impermeable membranes.

As shown, bellows pump 750 is fluidly connected to a check valve 752, which permits fluid flow away from bellows pump 750. Alternatively, the bellows pump may comprise a vent hole as in the embodiments of FIGS. 1A, 3A and 5A.

During operation, a liquid sample in placed into sample inlet 718, bellows pump 750 is depressed, either manually by a user or mechanically by an external device, and, then, bellows pump 750 is released. During depression of bellows pump 750, check valve 752, or a vent hole (not shown), prevents fluid flow from bellows pump 750 into first, second and third microfluidic channels 720, 730 and 740. Upon release of bellows pump 750, a negative fluid pressure is created in first, second and third microfluidic channels 720, 730 and 740 and the liquid sample is drawn into, and through, first, second and third microfluidic channels 720, 730 and 740 to first, second and third liquid barriers 726, 736 and 746 (as shown in FIG. 7C). As the liquid sample passes through first, second and third dried reagent zones 712, 714 and 716, the liquid sample hydrates the first, second and third reagents and mixing of the liquid sample and the first, second and third reagents occurs within first, second and third microfluidic channels 720, 730 and 740.

In addition, similar to FIGS. 1A, 2A and 5A, first, second and third microfluidic channels 720, 730 and 740 may comprise one or more optical viewing areas 760, 762 and 764 to enable visual verification that the liquid sample and the first, second and third reagents are flowing through first, second and third microfluidic channels 720, 730 and 740. In addition, optical viewing areas 760, 762 and 764 enable a user to visually observe reactions occurring between the liquid same and the first, second and third reagents.

Figure 8A:
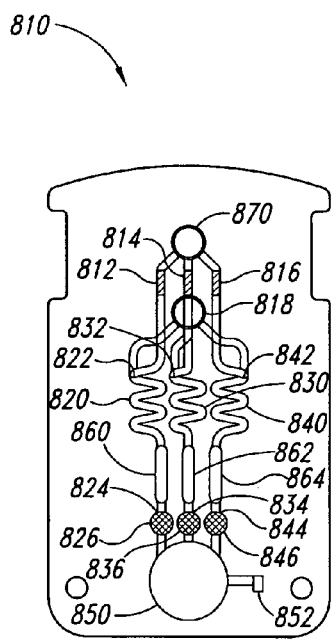
FIGS. 8A-8C are a series of cross-sectional views illustrating the operation of a seventh embodiment of a microfluidic device in accordance with aspects of the present invention.
Figure 8B:
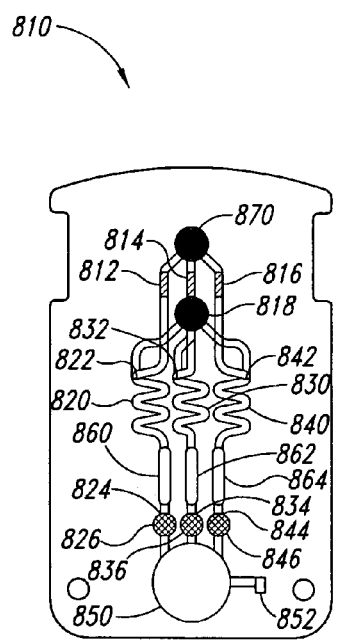
Figure 8C:
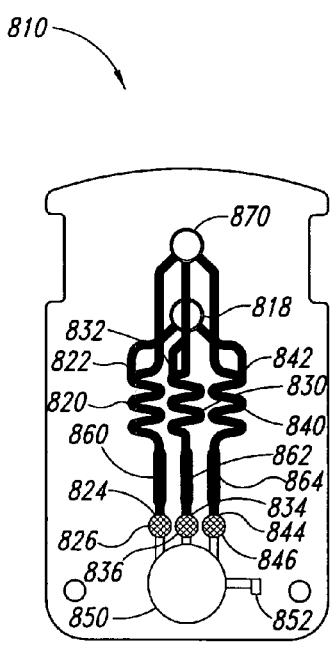

FIGS. 8A-8C are a series of cross-sectional views of a microfluidic device 810 illustrating the operation of a seventh embodiment of the invention. Microfluidic device 810 illustrated in FIG. 8A comprises a first microfluidic channel 820 having a first end 822 and a second end 824, a second microfluidic channel 830 having a first end 832 and a second end 834, and a third microfluidic channel 840 having a first end 842 and a second end 844. Sample inlet 818 is fluidly connected to first ends 822, 832 and 842 of first, second and third microfluidic channels 820, 830 and 840.

Device 810 further comprises a first dried reagent zone 812 wherein a first reagent in printed, a second dried reagent zone 814 wherein a second reagent is printed, and a third dried reagent zone 816 wherein a third reagent is printed. The first, second and third reagents may be printed during the manufacture of device 810 by methods such as ink jet printing, micro drop printing and transfer printing. As illustrated, device 810 also comprises a hydrating buffer inlet 870 for receiving a hydrating buffer. In alternate embodiments, the hydrating buffer may be loaded during the manufacture of device 810 and hydrating buffer inlet 870 may comprise, for example, a hydrating buffer blister pouch (not shown) containing the hydrating buffer. Such a blister pouch is adapted to burst, or otherwise release the hydrating buffer into device 810, upon actuation, such as, for example, depression of the blister pouch either manually by a user or mechanically by an external device.

As illustrated, hydrating buffer inlet 870, and each of first dried reagent zone 812, second dried reagent zone 814, and third dried reagent zone 816 are fluidly connected to first ends 822, 832 and 842 of first, second and third microfluidic channels 820, 830 and 840. Bellows pump 850 is fluidly connected to second ends 824, 834 and 844 of first, second and third microfluidic channels 820, 830 and 840, and first, second and third liquid barriers 826, 836 and 846 are interposed between bellows pump 850 and second ends 824, 834 and 844 of first, second and third microfluidic channels 820, 830 and 840. First, second and third liquid barriers 826, 836 and 846 are gas permeable and liquid impermeable membranes.

As shown, bellows pump 850 is fluidly connected to a check valve 852, which permits fluid flow away from bellows pump 780. Alternatively, the bellows pump may comprise a vent hole.

During operation, a liquid sample in placed into sample inlet 818 and a hydrating buffer is placed into hydrating buffer inlet 870. (In the alternate embodiment, wherein hydrating buffer inlet 870 comprises a hydrating buffer blister pouch containing the hydrating buffer, operating is commenced by placing a liquid sample into sample inlet 818 and manually actuating the blister pouch to release the hydrating buffer.) Bellows pump 850 is then depressed, either manually by a user or mechanically by an external device, and, then, bellows pump 850 is released. During depression of bellows pump 850, check valve 852, or a vent hole (not shown), prevents fluid flow from bellows pump 850 into first, second and third microfluidic channels 820, 830 and 840. Upon release of bellows pump 850, a negative fluid pressure is created in first, second and third microfluidic channels 820, 830 and 840 and the liquid sample and the hydrating buffer are drawn into, and through, first, second and third microfluidic channels 820, 830 and 840 to first, second and third liquid barriers 826, 836 and 846 (as shown in FIG. 8C). As the hydrating buffer passes through first, second and third dried reagent zones 812, 814 and 816, the hydrating buffer hydrates the first, second and third reagents and, subsequently, mixing of the liquid sample and the first, second and third reagents occurs within first, second and third microfluidic channels 820, 830 and 840.

In addition, similar to FIGS. 1A, 2A, 5A and 7A, first, second and third microfluidic channels 820, 830 and 840 may comprise one or more optical viewing areas 860, 862 and 864 to enable visual verification that the liquid sample and the first, second and third reagents are flowing through first, second and third microfluidic channels 820, 830 and 840. In addition, optical viewing areas 860, 862 and 864 enable a user to visually observe reactions occurring between the liquid same and the first, second and third reagents.

From the foregoing, and as set forth previously, it will be appreciated that, although specific embodiments of the invention have been described herein for purposes of illustration, various modifications may be made without deviating from the spirit and scope of the invention. A person of ordinary skill in the art will appreciate that a plurality of microfluidic channels, inlets, valves, membranes, pumps, liquid barriers and other elements may be arranged in various configurations in accordance with the present invention to manipulate the flow of a fluid sample in order to prepare such sample for analysis. Accordingly, the invention is not limited except as by the appended claims.

What is claimed is:

1. A microfluidic device for analyzing a liquid sample, comprising:
    a first microfluidic channel having a first end and a second end;
    a second microfluidic channel having a first end and a second end;
    a third microfluidic channel having a first end and a second end;
    a sample inlet, fluidly connected to the first ends of the first, second and third microfluidic channels, for receiving the liquid sample;
    a hydrating buffer inlet, fluidly connected to the first ends of the first, second and third microfluidic channels, for receiving a hydrating buffer;
    a bellows pump fluidly connected to the second ends of the first, second and third microfluidic channels;
    a first dried reagent zone wherein a first reagent is printed, fluidly connected between the hydrating buffer inlet and the first end of the first microfluidic channel;
    a second dried reagent zone wherein a second reagent is printed, fluidly connected between the hydrating buffer inlet and the first end of the second microfluidic channel; and
    a third dried reagent zone wherein a third reagent is printed, fluidly connected between the hydrating buffer inlet and the first end of the third microfluidic channel.

2. The microfluidic device of claim 1 wherein the hydrating buffer inlet comprises a hydrating buffer blister pouch containing the hydrating buffer.

3. The microfluidic device of claim 1 wherein the bellows pump comprises a vent hole.

4. The microfluidic device of claim 1, further comprising a check valve fluidly connected to the bellows pump, wherein the check valve permits fluid flow away from the bellows pump.

5. The microfluidic device of claim 1 wherein the first microfluidic channel further comprises one or more optical viewing areas.

6. The microfluidic device of claim 1 wherein the second microfluidic channel further comprises one or more optical viewing areas.

7. The microfluidic device of claim 1 wherein the third microfluidic channel further comprises one or more optical viewing areas.

8. The microfluidic device of claim 1 wherein the liquid sample comprises a blood sample, the first reagent comprises antibody-A, the second reagent comprises antibody-B, and the third reagent comprises antibody-D.

* * * * *